US006760107B1

(12) United States Patent
Drake

(10) Patent No.: US 6,760,107 B1
(45) Date of Patent: Jul. 6, 2004

(54) DETECTION OF SCATTERED LIGHT FROM PARTICLES

(75) Inventor: David A. Drake, Escondido, CA (US)

(73) Assignee: PointSource Technologies, LLC, Escondido, CA (US)

( * ) Notice: Subject to any disclaimer, the term of this patent is extended or adjusted under 35 U.S.C. 154(b) by 104 days.

(21) Appl. No.: 10/272,869

(22) Filed: Oct. 16, 2002

Related U.S. Application Data

(60) Provisional application No. 60/372,684, filed on Apr. 12, 2002.

(51) Int. Cl.[7] ............................................... G01N 21/00
(52) U.S. Cl. ...................... 356/338; 356/356; 356/343; 356/457
(58) Field of Search ................................ 356/338, 337, 356/340, 343, 457

(56) References Cited

U.S. PATENT DOCUMENTS 6,313,908 B1   11/2001   McGill et al.

Primary Examiner—Frank G. Font
Assistant Examiner—Roy M. Punnoose
(74) Attorney, Agent, or Firm—Leon D. Rosen

(57) ABSTRACT

An improvement is provided for a system that identifies particles such as microorganisms in fluid by directing a laser beam (52) forwardly through a tiny detect zone (46) in the fluid and detecting the pattern of light scatter by a particle as it passes through the detect zone. The improvement includes a holographic optical element (60) positioned forward of the detect zone to intercept light scattered in multiple directions by the particle. The holographic optical element is divided into discrete areas, or sections, that each directs intercepted scattered light toward a selected photodetector (74, 90, 92) of a linear array (62) of photodetectors. A converging lens (106) reduces the required diffraction angles of the sections of the holographic optical element. This arrangement avoids the need to custom mount and connect numerous individual photocells, and enables simplified high speed readout of the photodetectors.

19 Claims, 4 Drawing Sheets

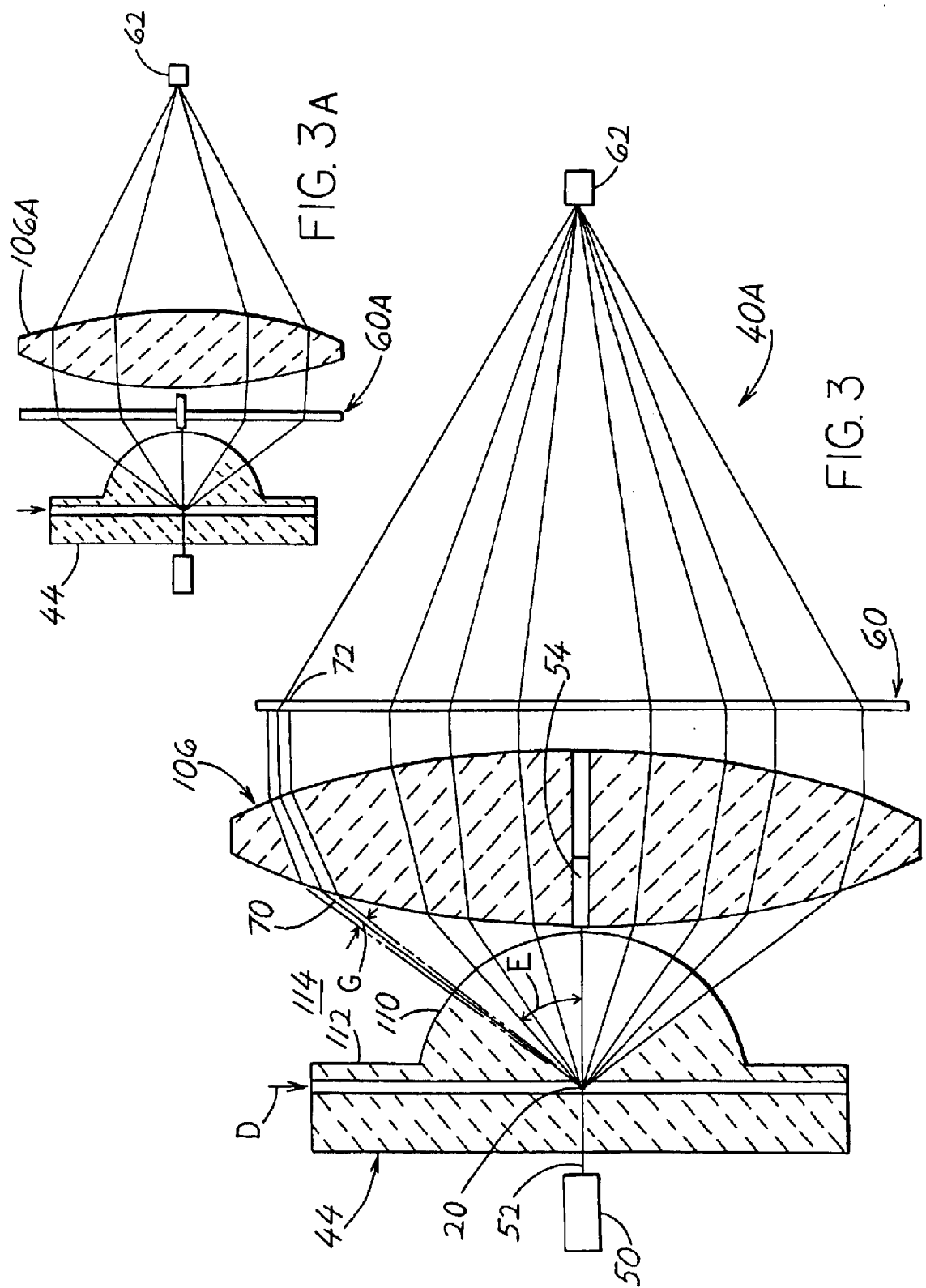

DETECTION OF SCATTERED LIGHT FROM PARTICLES

CROSS-REFERENCE TO RELATED APPLICATION

Applicant claims the benefit of U.S. Provisional patent application Ser. No. 60/372,684 filed Apr. 12, 2002.

BACKGROUND OF THE INVENTION

Microscopic particles such as particular species of bacteria lying in a fluid such as water or air, can be identified by detecting their pattern of light scatter when they pass through a light beam such as a laser beam. A plurality of photodetectors can be positioned to detect light scattered in different directions from a small detect zone lying along the laser beam. The outputs of the photodetectors are delivered to a computer that compares the pattern of light scatter for an unknown particle that is passing through the detect zone, to the patterns of a list of known species of particles, usually microorganisms, to determine whether the unknown particle is a member of one of the listed species.

Previously, applicant custom mounted the multiple photodetectors on a frame that could position photodetectors to detect light scattered in different directions and at different angles from the forward direction of the laser beam. Such a frame and detectors can be awkward and expensive to build and connect to. Furthermore, such a setup can result in a rat's nest of wires extending from the multiple photodetectors to a cable leading to the computer. The large number of custom terminated wires can result in reduced reliability of electrical connections and considerable signal losses along some of the wires. A system that avoided the need for such difficult mounting and such rat's nest of wires, would be of value.

SUMMARY OF THE INVENTION

In accordance with one embodiment of the present invention, an apparatus and method are provided that improve operation of a system for identifying microscopic particles in a fluid by directing a laser beam through the fluid and detecting light scattered in multiple directions by a particle passing through the detect zone. Instead of mounting individual detectors on a frame, so each detector can detect light scattered in a predetermined direction from the detect zone, and providing multiple wires leading from each detector to an amplifier that connects to a computer, applicant provides a holographic optical element and at least one linear array of photodetectors such as CCDs (charge coupled devices). The holographic optical element is constructed with multiple areas, or sections, that are each constructed to direct light received from the direction of the detect zone, toward a selected one of the photodetectors of the linear array. A converging lens preferably lies immediately forward or rearward of the holographic optical element. Only a single holographic optical element is required to intercept light scattered in multiple directions within a wide angle from the detect zone. By directing the scattered light to selected photodetectors of a linear array, applicant can use available linear arrays of photodetectors such as CCDs. The linear array not only simplifies mounting of photodetectors and avoids multiple custom connections and a rat's nest of wire which all degrade performance, but enables rapid readout.

The holographic optical element can be constructed with sections that each intercept light scattered in a particular circumferential direction and at a particular angle to the forward direction of the laser beam, to mimic the detection of light by individually mounted photodetectors of applicant's prior systems. In another arrangement, the holographic optical element takes advantage of the fact that the element can direct light from an area of any shape on the hologram to a selected photodetector, to make detections that facilitate the identification of the unknown particle. In one arrangement, the holographic optical element is divided into sections that are each in the shape of a narrow ring. In another arrangement, one part of the hologram forms sections that are parts of rings, while another part forms multiple pie-shaped sections. In another arrangement, the holographic optical element is divided into multiple small sections, or areas that each direct intercepted light to a different photodetector. Substantially all locations in each small area lie within about 5° of its center. The photodetector outputs can be combined to simulate rings, pie-shaped sections, etc.

A linear array of CCDs forms an image scanner, to deliver the outputs of the detectors of the array sequentially to the computer. This simplifies connection of the linear array to the computer, especially if a large number of detectors of the linear array are used.

The novel features of the invention are set forth with particularity in the appended claims. The invention will be best understood from the following description when read in conjunction with the accompanying drawings.

BRIEF DESCRIPTION OF THE DRAWINGS

FIG. 3 is a sectional view of a portion of the system of FIG. 2, but modified to include a converging lens.

FIG. 3A is a sectional view of a portion of the system of FIG. 2, but with the converging lens positioned forward of the holographic optical element instead of behind it.

DESCRIPTION OF THE PREFERRED EMBODIMENTS

Figure 1:
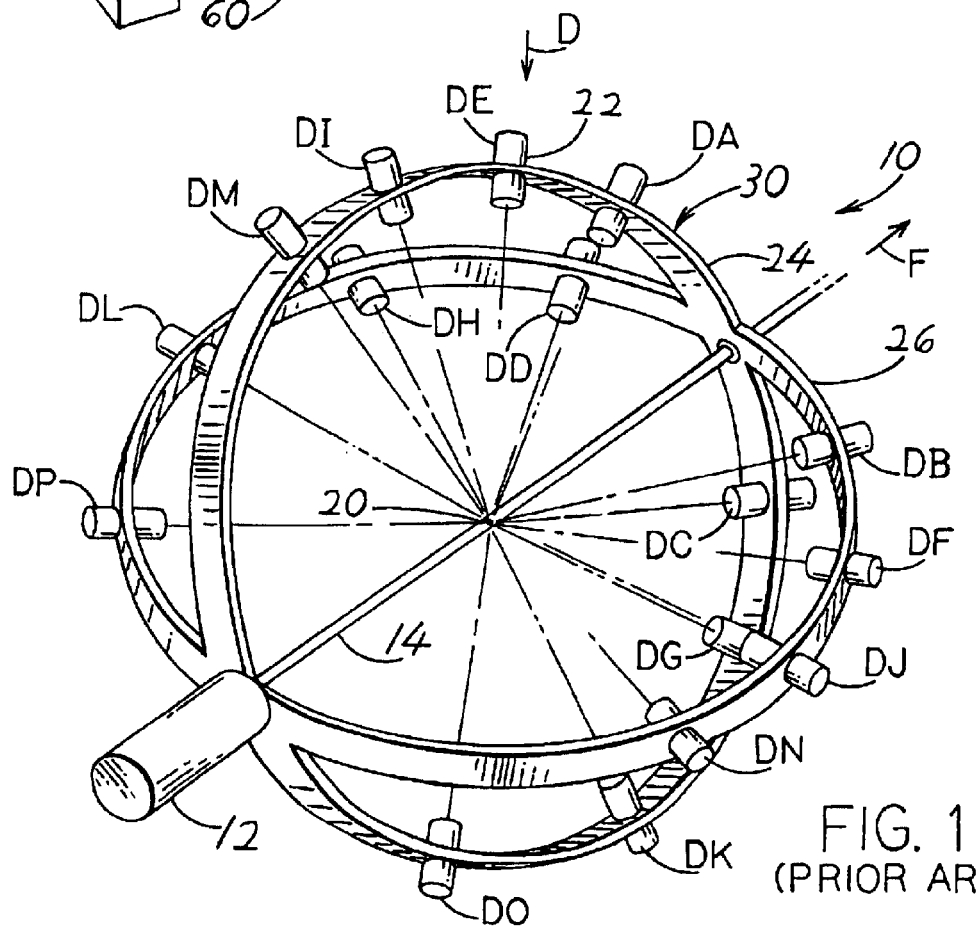
FIG. 1 is an isometric view of a prior apparatus that applicant has used to identify microscopic particles in a fluid.

FIG. 1 illustrates a portion of a system 10 that applicant previously designed for the detection and identification of microscopic particles, and especially microorganisms, in a fluid such as water or air. The system includes a laser 12 that directs a laser light beam 14 in a forward direction F through a quantity of water that is flowing in a downward direction D. A small volume along the laser beam is designated as a detect zone 20. Multiple photodetectors 22 are provided that are aimed at the detect zone 20, to each detect only light originating from the detect zone. FIG. 1 shows sixteen photodetectors labeled DA through DP that are mounted on two rings 24, 26 of a frame 30. Each photodetector detects lights within an angle of about 2° that originates from the detect zone 20. The outputs of the sixteen photodetectors are delivered through wires (not shown) to a computer. The computer compares the pattern of light scattering from an unknown particle entering the detect zone 20, to light scatter patterns for a known group of species of microorganisms, and can indicate if the light scatter pattern for the unknown particle indicates that it is one of the group of microorganisms for which the computer has been programmed. Applicant uses statistical pattern recognition to establish that an unknown particle is a member of a class of particles of interest (e.g. species of microorganisms).

It can be appreciated that the custom frame 30 involves some complexity in its construction and accurate mounting, to assure that each photodetector detects only light originated from the detect zone 20. Also, it can be appreciated that if four or five wires are connected to each photodetector and the wires are extended to the computer, that this would create a "rat's nest" of wires near the detectors. Such a large number of wires which are connected to the photodetectors by custom connections such as solder joints, results in lower reliability and the possibility that there are significant signal losses along the wires leading to the computer.

Figure 2:
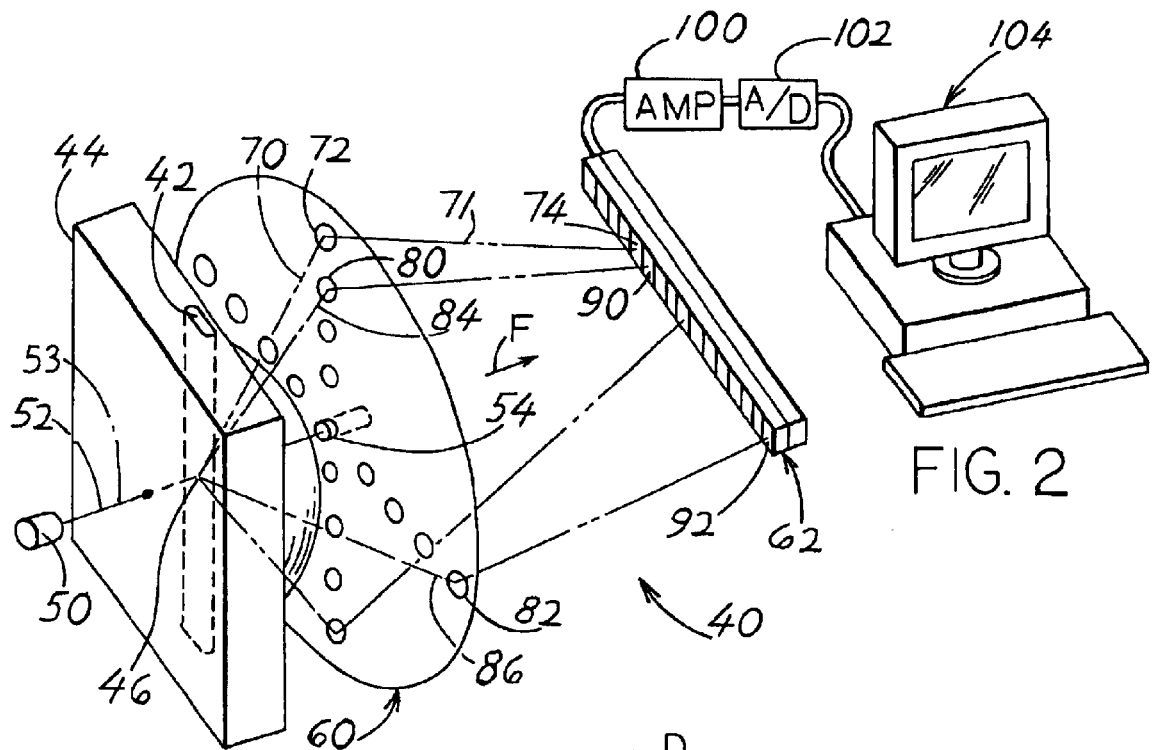
FIG. 2 is an isometric view of a system of the present invention, that uses a holographic optical element, a linear array of photodetectors and an image scanner to enable the identification of microscopic particles in a fluid.

FIG. 2 illustrates a complete system 40 in accordance with one embodiment of the invention. Fluid such as water which carries the microscopic particles, moves along a passage 42 of a glass carrier 44. The detect zone 46 lies along the passage 42, so that particles can pass through the detect zone. A laser 50 directs a laser beam 52 in a forward direction F along a beam axis 53 to pass through the detect zone 46 and to a trap 54 that traps substantially all light that has not been scattered (and that usually constitutes more than 99% of the laser beam energy). In one example, the laser beam 52 has a horizontal width of 0.5 mm and an average vertical thickness of 0.1 mm, and the detect zone occupies only a portion of the laser beam that extends along a length of 1 mm.

Instead of placing multiple photodetectors to intercept the scattered light beams, applicant uses a holographic optical element 60 to intercept the scattered light, and uses a linear array of photodetectors 62 to detect the light and generate an electrical signal having an amplitude corresponding to the amplitude of the detected light. Such an array has at least five separate photodetectors, and usually many more. CCDs are readily available with between 512 and 2048 pixels, each forming a photodetector. FIG. 2 shows a narrow light ray 70 scattered from the detect zone 46 by a particle therein. The holographic optical element has an active section 72 that is constructed to divert light received from the direction of the zone 46, to a selected photodetector 74 of the linear array 62. The holographic optical element has additional sections such as 80 and 82 that direct light beams 84, 86 respectively to photodetectors 90, 92. Areas between the active sections are inactive in that they do not direct light received from the detect zone to one of the photodetectors. Such inactive sections may be opaque. The outputs of the photodetectors of the array 62 exit the array in a rapid sequence, and the outputs pass through an amplifier 100 and an analog-to-digital converter 102 to a computer 104 that indicates whether the detected particle is a member of a known group of species of particles, especially of microorganisms.

FIG. 3 shows some details of a system 40A similar to that of FIG. 2. Applicant constructs the carrier 44 with a largely spherical lens 110. The center of curvature of the lens is located at or slightly behind the detect zone 20 so the lens serves as neither a converging nor diverging lens (although a converging lens could be useful). If the front surface of the carrier 44 were flat, as with a continuation of the flat top and bottom surfaces at 112, then light scattered from the detect zone 20 at an angle E from the forward direction of the beam 52, would be internally reflected at the interface of the carrier surface 112 and air 114 in the environment, for an angle E of more than about 41°. The spherical lens allows light scattered at any angle to the lens, to pass out into the atmosphere where the holographic element is located. Also, the largely spherical lens 110 makes the path of the light easier to determine.

In FIG. 3, applicant has added a condensing, or converging lens 106 between the lens 110 and the holographic optical element. A converging lens reduces the angle of spread, or collimates, or converges, light rays. FIG. 3 shows that the light beam 70 is refracted by the lens 106 toward the forward direction, and is refracted by the section 72 of the holographic optical element 60 to a selected photodetector of the linear array 62. Although the system can be used without the converging lens, this results in the element sections being required to refract light by large angles (e.g. about 80° for beam 70). This requires finer resolution for the holographic sections, and such holographic optical element is more difficult to make. With the lens 106, the holographic sections refract light at smaller angles (e.g. about 30° for beam 70). FIG. 3A shows a system where the converging lens 106A lies forward of the holographic optical element 60A instead of behind it.

The holographic optical element 60 of FIG. 2 is shown constructed so each refracting section 72 refracts, or redirects light from one path 70 to another 71 to fall on the linear array of photodetectors, only for light emanating from the detect zone 46 within about 2° of the axis 70 of the light beam. As shown in FIG. 3, the light intercepted by the holographic section 72 subtends a narrow angle G on the order of 4°. FIG. 2 shows that the particular holographic optical element 60 has sixteen of such sections similar to section 72, that each diffracts light received within a small angle to one of the detectors of the linear array 62. The rest of the element 60 is opaque or directs light away from the linear array 62. The purpose of this arrangement is to have the element 60 mimic the detections by the sixteen photocells 22 of FIG. 1.

With the use of a holographic optical element, applicant can make detections in different ways that would not be practical with an arrangement such as shown in FIG. 1 where a limited number of narrow acceptance angle photodetectors 22 are spaced apart and each individually mounted on a frame.

Figure 4:
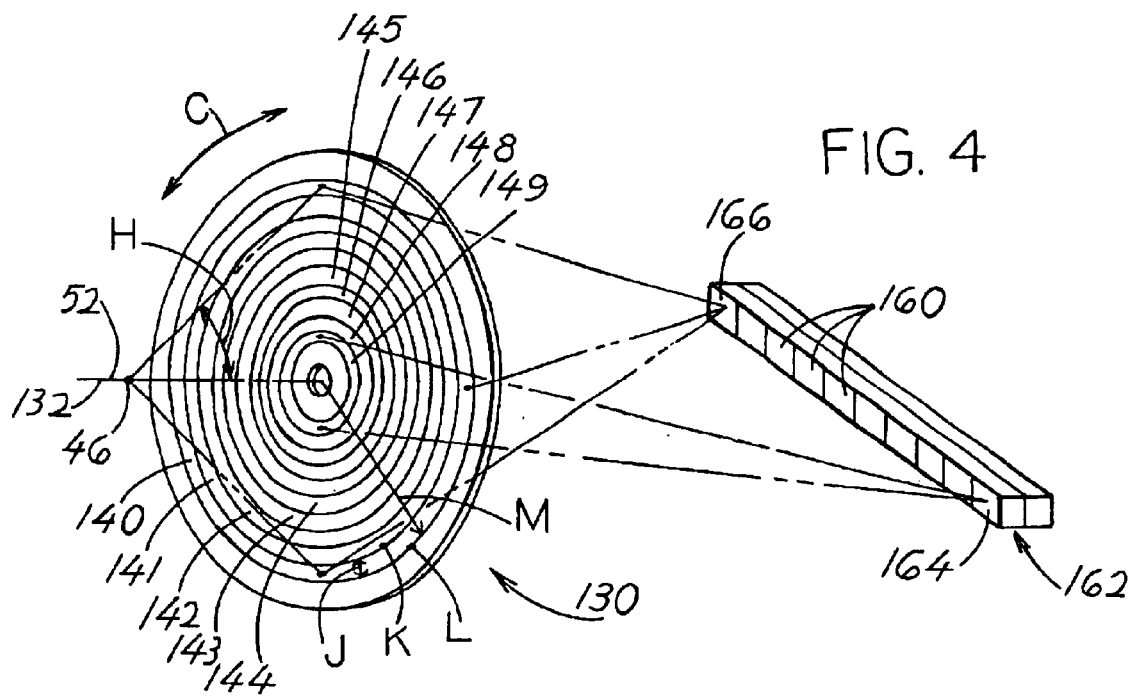
FIG. 4 is an isometric view of a portion of a system similar to that of FIG. 3 with a modified holographic optical element which enables the detection of the scatter angle of light from the detect zone with respect to the forward direction of a laser beam, for each of multiple angle.

FIG. 4 shows a holographic optical element 130 which takes advantage of the fact that, for some particles, the most distinguishing feature is the angle H with respect to an axis 132 of the laser beam, at which light is scattered from the detect zone 46, regardless of the circumferential direction C around the laser beam 52. The holographic optical element is formed with ten ring sections (of 360° each), or rings 140–149. Each ring is concentric with the beam direction axis 132 and refracts light scattered within a certain angle H from the beam direction 52 (through a condensing lens, not shown in FIG. 4) to a selected one of the detectors 160 of the linear array 162. In one example, ring 149 intercepts and diffracts light falling within an angle of 10° to 16° from the beam direction 52 to a selected photodetector 164. The outermost diffracting ring 140 diffracts scattered light received within an angle of 62° to 70° from the beam direction 52 to another photocell 166. Each of the other rings 141–148 intercepts and diffracts light within a range of 6° to a selected one of the detectors. Each ring has a radial width J between its inner and outer ring edges K, L, which is no more than 20% of the radial distance M to the outer ring edge, for rings that lie beyond ring 146.

Figure 6:
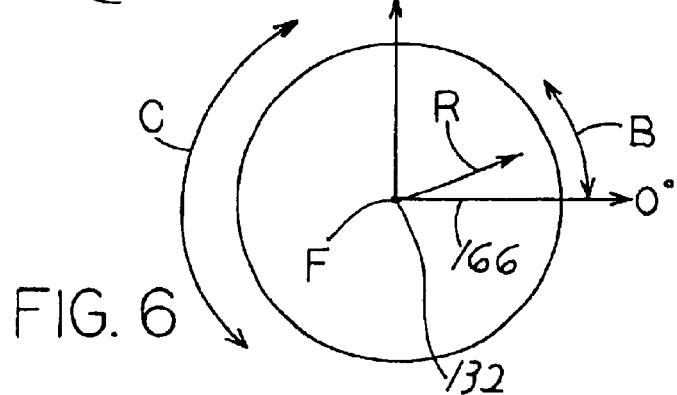
FIG. 6 is a diagram for identifying scatter angles.

FIG. 6 is a diagram showing a laser beam direction F which extends into the paper, and two angular coordinates. A first coordinate is the angle H of FIG. 4, from the axis or beam direction F. This determines the radius, or distance R at which scattered light falls on the holographic optical element (which is spaced a known distance from the detect zone 46). The other coordinate is the circumferential angle B in the circumferential direction C from a ray 166 of zero angle extending perpendicular to the beam axis.

Figure 5:
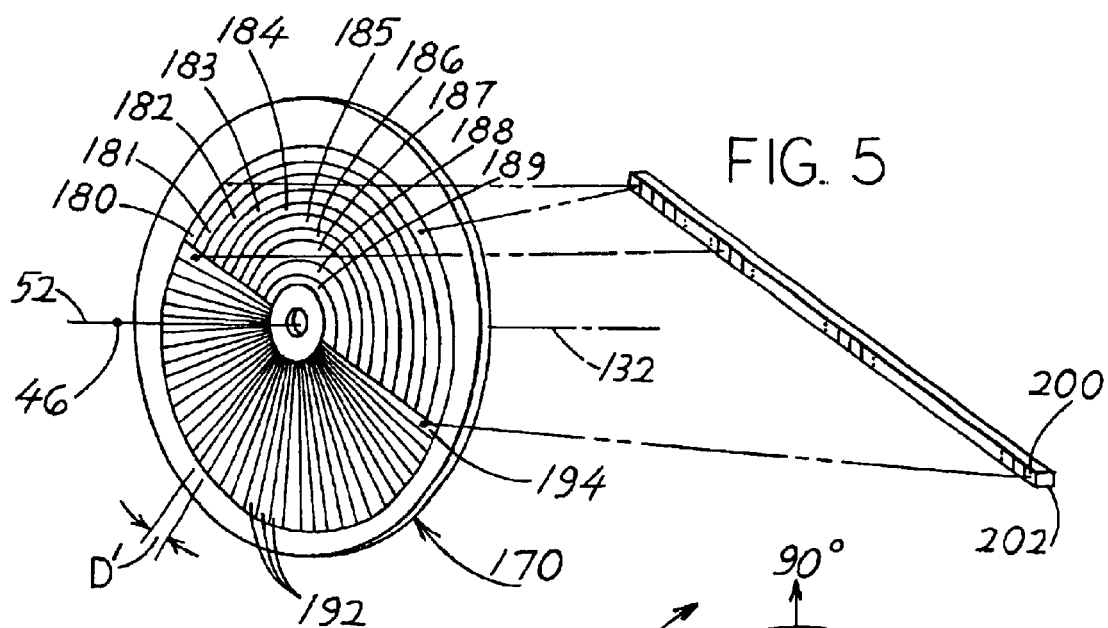
FIG. 5 is an isometric view of a portion of a system similar to that of FIG. 4, but with only half of the hologram used to identify the angle of scatter light from the beam direction, with the other half of the hologram being used to detect the circumferential direction of light scatter regardless of the angle from the beam direction.

FIG. 5 illustrates another holographic optical element 170 which enables the detection of scattering at different axial angles H from the direction of the laser beam, and which also enables the detection of scattering in different circumferential directions. The element 170 has its upper half divided into ten half-rings 180–189 that each extends about 180° about the axis 132 that is coincident with the laser beam 52. The element has a lower half that is divided into thirty-six pie-shaped radial sections 192, each section extending in a different circumferential direction and each section subtending an angle D' of no more than about 12° about the axis 190. Thus, all light scattering onto the particular section 194 is diffracted (through a condensing lens, not shown in FIG. 5) into a particular detector 200 or group that includes a limited number of detectors, of the linear array of detectors 202. The holographic optical element 170 of FIG. 5 therefore enables the detection of the angle of scattering of light from the axis 132 along ring-shaped section areas 180–189. The element also enables detection of the circumferential direction of scattering of light by the thirty-six elements 192.

The construction of a holographic optical element can be accomplished in many ways. A traditional method suggested by early experimenters, is to split a coherent beam, such as is obtained from a laser, into two beams parts, one of which originates from the detect zone 46 and which illuminates a particular section of the element, and to direct another part of the split beam from the location of the desired photodetector on the linear array, at the same section of the element. The element may comprise a film or glass plate with a photosensitive coating or film on it. The portion of the film outside the section that is to diffract light toward a particular photodetector is masked. This is continued for all other sections of the element that are to diffract light. The photographic plate is developed, and can be photographically duplicated. At present, holographic optical elements are most easily created by a computer-controlled illumination source, which creates the desired fresnel patterns.

U.S. Pat. No. 6,313,908 by McGill. et al., owned by NASA, describes a holographic optical element that detects a wide beam of light containing many different wavelengths (a spectral distribution of light), so each wavelength is focused onto a different point. The points may be an array of CCDs.

Figure 7:
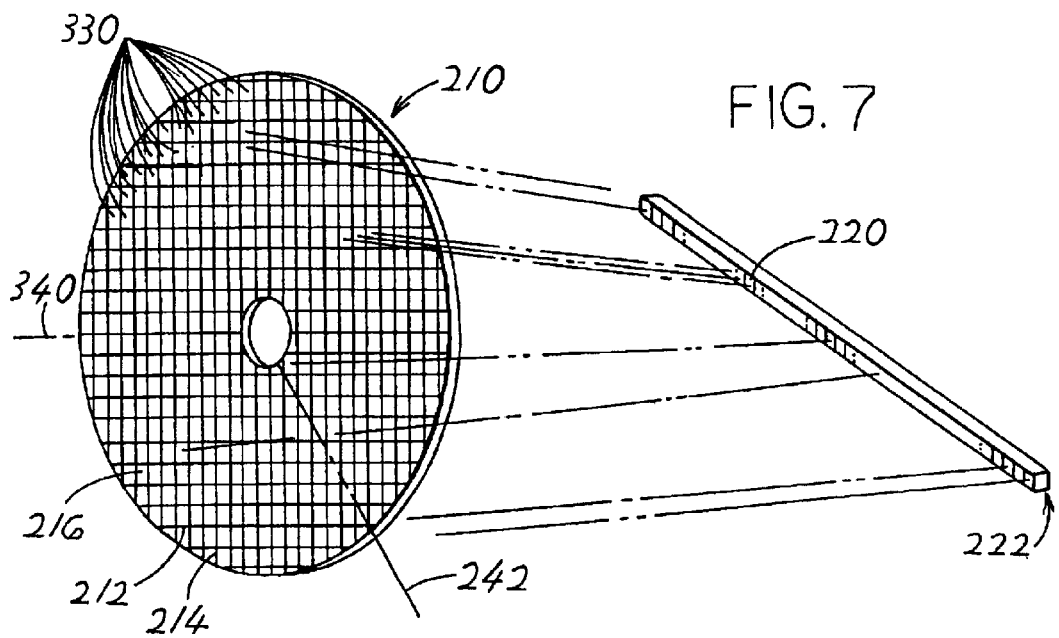
FIG. 7 is an isometric view of a portion of a system similar to that of FIG. 3, with a modified holographic optical element divided by perpendicular lines into multiple small sections.
Figure 8:
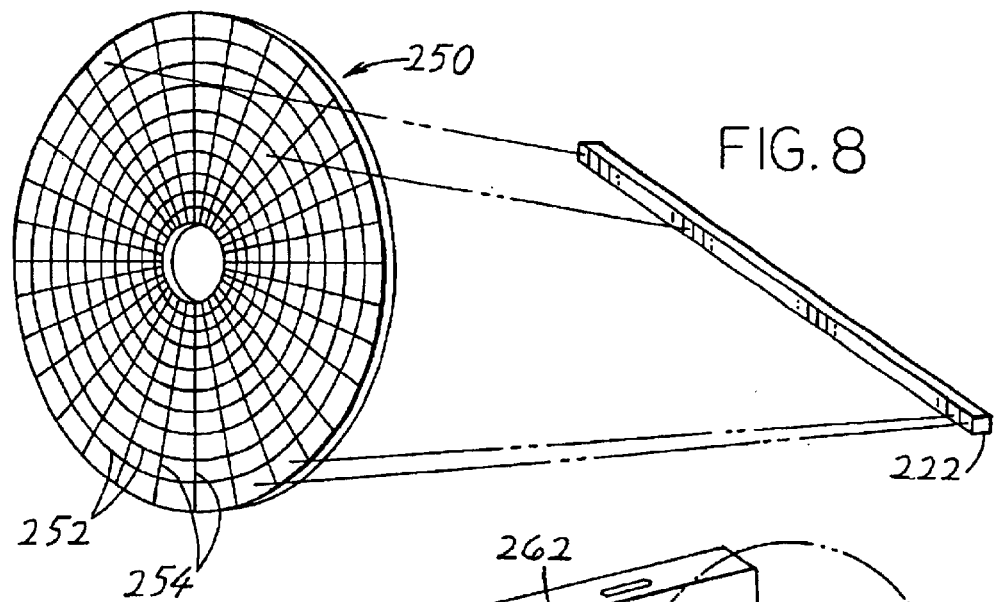
FIG. 8 is an isometric view of a portion of a system similar to that of FIG. 3, with a modified holographic optical element divided by lines radial and circumferential to the axis into multiple small sections.

FIG. 7 illustrates a holographic element 210 that is divided by horizontal and vertical lines 212, 214 into numerous sections 216. Each section receives light scattered within a small angle of no more than about 4°, and preferably no more than 2° that originates at the detect zone, and may be referred to as a hologram pixel. Each section directs the light (preferably through a condensing lens) to one of the detectors 220 of an array 222. The outputs of selected detectors can be combined to represent the output of one photodetector that receives light from a section (composed of a plurality of hologram pixels. For example, the output of all detectors that detect light from sections such as 330, represent a ring extending 45° about the axis 340. The outputs of all detectors that detect light from sections close to line 242 represent the output of a pie-shaped section. FIG. 8 illustrates a holographic optical element 250 divided into similar small sections by circumferential lines 252 and radial lines 254.

Figure 9:
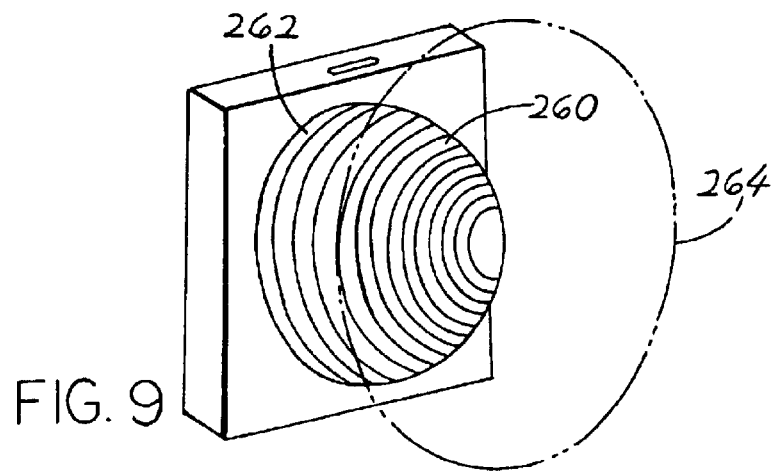
FIG. 9 is an isometric view of a portion of another system, wherein the holographic optical element is a layer lying on the spherical lens.

FIG. 9 illustrates a holographic optical element 260 in the form of a layer lying on the surface of a convex lens 262. The lens can be similar to the lens 110 of FIG. 3 which forms the front of a carrier. A converging lens 264 lies in front of the holographic layer at 260.

Although a single holographic optical element can be used, such as shown in FIGS. 2, 4–5 and 7–8, it is possible to use more than one holographic element. One or more additional of such elements can be useful to diffract light scattered at a large angle, such as more than about 70° or 80° to the beam direction, to detectors of an array, or even to diffract light scattered backward, that is, more than 90° to the forward direction of the laser beam. It is noted that applicant has illustrated a single linear array of detector elements, which is most likely implemented by a CCD (charge coupled diode) array. In such array, all CCD elements lie substantially in a single plane, and in substantially a single line. Such a linear array can be scanned at high rates of more than one thousand CCD elements per second. It is noted that applicant usually requires fewer than 1024 photodetectors, and this can be accomplished by taking the outputs of perhaps ten to fifty CCD elements as the output of a single photodetector. If necessary, two or more linear arrays can be used, whose outputs may be sequentially scanned. It is also possible to use a two dimensional array of CCD elements, all lying in substantially a single plane, but a scanning rate for such elements is commonly only 60 scans per second. In applicant's apparatus, where water may flow at a substantial velocity such as 8 cm/second, it is desirable to be able to detect particles that pass through the detect zone during a period of 1/1000th second.

Thus, the invention provides an improved apparatus and method for identifying microscopic particles in a fluid by detecting scatter patterns of particles. The improvement includes a holographic optical element that is positioned so different sections of it intercept light scattered in different directions from a detect zone through which a laser beam and particles to be detected pass, and each section directs (refracts or reflects) the intercepted light toward a different photodetector. A converging lens preferably lies forward or rearward of the holographic optical element. At least one linear array of photodetectors, such as a CCD with line array of CCD detectors, charge injection device, discrete silicon detector array, image intensified detector, etc. is positioned in the vicinity of the holographic optical element. The linear array can be progressively scanned to provide a sequence of signals representing the outputs of the different detectors of the array, to an analog-to-digital converter, whose output is delivered to the computer. The output of a CCD is automatically sequential. In one arrangement, the holographic optical element has isolated largely circular small sections mimicking the beams detected by the use of individual photodetectors that are separately mounted on a frame. In another arrangement, the holographic optical element has sections in the forms of rings concentric with the axis of the element. The rings may occupy only a fraction of a 360° continuous ring, but each preferably occupies at least 45° of such continuous ring. The holographic optical element may also include pie-shaped sections for detecting lights scattered all in the same circumferential direction from the detect zone, but at different angles to the beam direction. Other holographic optical elements may be divided into multiple squares, a pattern of rings divided by radial lines, etc. to provide small sections that each extend no more than about 4° from the middle of the section. The outputs of selected groups of detectors can be added together so each group represents a ring, etc.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. Apparatus for use in a system for identifying microscopic particles in a fluid, which includes a source that generates a light beam, wherein the light beam travels in a forward direction along a beam axis that passes through a small detect zone, with light of the light beam being scattered in different directions from said detect zone by a particle that enters said detect zone, comprising:

a plurality of photodetectors;

a holographic optical element positioned to intercept light scattered in each of a plurality of different directions from a particle in said detect zone;

said holographic optical element having a plurality of separate active holographic sections, each active holographic section being formed to direct light received from the direction of said detect zone, toward a selected group of at least one of said photodetectors.

2. The apparatus described in claim 1 wherein:

said plurality of photodetectors all lie in substantially a common plane.

3. The apparatus described in claim 1 wherein:

said plurality of photodetectors are arranged in a linear array of at least five photodetectors.

4. The apparatus described in claim 1 including:

a converging lens that lies between said detect zone and said holographic optical element.

5. The apparatus described in claim 1 including:

a converging lens that lies between said holographic optical element and said plurality of detectors.

6. The apparatus described in claim 1 wherein:

a plurality of said active holographic sections, each occupies an area lying within about 4° of the axis of a scattered beam of light that originates from the center of said detect zone and that intersects the middle of the section.

7. The apparatus described in claim 1 wherein:

a plurality of said active holographic sections, each defines a ring-shaped area that has inner and outer ring edges that are both centered on said beam axis.

8. The apparatus described in claim 7 wherein:

a radial distance between said inner and outer ring edges of each of a plurality of said rings is no more than 20% of the radial distance between the outer ring edge and the beam axis.

9. The apparatus described in claim 1 wherein:

at least a portion of said holographic optical element is divided into a plurality of ring sections that each forms one of said active holographic sections, said ring sections each having a center of curvature lying on said beam axis, each ring section extending at least 45° about said beam axis, and said ring sections have different radii of curvature and are each formed to direct light received from said detect zone to a different one of said detectors.

10. The apparatus described in claim 1 wherein:

at least a portion of said holographic optical element is divided into a plurality of largely pie-shaped radial sections wherein the center of the pie section lies on said beam axis, and each radial section is formed to direct light received from said detect zone to a different one of said photodetectors.

11. The apparatus described in claim 1 wherein:

at least a portion of said holographic optical element is divided into a plurality of largely pie-shaped radial sections that each lies within a circumferential angle centered on said beam axis, and that each has radially inner and outer ends that are radially spaced form said beam axis, the average circumferential width of each radial section being less than half the radial distance between said inner and outer ends;

each of said radial sections of said holographic optical element is formed to direct light received from said detect zone to a different one of said photodetectors.

12. The apparatus described in claim 1 including:

a carrier which has a passage through which said fluid can pass, said detect zone lying in said passage;

said carrier has a carrier front wall of transparent solid material which lies between said detect zone and said holographic optical element, said carrier front wall having a rear face forming a surface of said passage and said front wall having a convex front face forming a convex lens;

said holographic sections are each formed to direct light passing along a path from said detect zone to said element, toward the selected one of said detectors.

13. The apparatus described in claim 12 wherein:

said holographic optical element comprises a convexly curved layer that lies facewise on said convex front face of said lens.

14. Apparatus for detecting light scattered from a detect zone that lies along the intersection of a narrow coherent light beam and a quantity of fluid that contains microscopic particles, comprising:

a plurality of photodetector means;

a holographic optical element means positioned to intercept light of said light beam that is scattered from said detect zone, said holographic optical element means having sections each for directing light received from said detect zone to a different group of at least one of said photodetectors.

15. The apparatus described in claim 14 including:

converging lens means lying along the paths of light extending from said detect zone to said photodetector means, for reducing the angles by which said sections must retract light.

16. A method for identifying microscopic particles in a fluid by directing a laser beam along an axis and forwardly through a detect zone and passing some of the fluid with the particles through the detect zone to cause the particles to scatter light of the laser beam, and identifying particles that are of a certain species by their scatter patterns, comprising:

positioning a holographic optical element behind said detect zone, wherein said element has a plurality of active sections;

positioning an array of photodetectors in the vicinity of said element;

directing light that scatters from said detect zone in each of a plurality of particular directions to reach particular ones of said active sections, from each of said particular active sections toward a particular at least one of said photodetectors.

17. The method described in claim 16 wherein:

a plurality of said active sections each comprises at least part of a ring-shaped area having inner and outer ring edges both centered on said axis and with the radial distance between the ring edges being no more than 20% of the radius from said axis to the largest of said ring-shaped areas.

18. The method described in claim 16 wherein:

a plurality of said active sections each comprises at least part of a pie-shaped section that lies within about 6° of a radial line that extends radially from said axis.

19. The method described in claim 16 including:

positioning a converging lens between said detect zone and said photodetectors, to reduce the angles by which said sections of said holographic optical element must diffract light to reach said photodetectors.

* * * * *